US006539265B2

United States Patent
Medhkour et al.

(10) Patent No.: US 6,539,265 B2
(45) Date of Patent: Mar. 25, 2003

(54) APPARATUS FOR RF INTRALUMINAL REDUCTION AND OCCLUSION

(75) Inventors: Adel M. Medhkour, Brooklyn Park, MN (US); Michael F. Hoey, Shoreview, MN (US); Peter M. J. Mulier, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/848,487

(22) Filed: May 3, 2001

(65) Prior Publication Data

US 2001/0023365 A1 Sep. 20, 2001

Related U.S. Application Data

(62) Division of application No. 09/304,681, filed on May 4, 1999, now Pat. No. 6,327,505.
(60) Provisional application No. 60/084,580, filed on May 7, 1998.

(51) Int. Cl.[7] .............................. A61N 1/06; A61N 1/18
(52) U.S. Cl. .................... 607/99; 607/105; 607/113; 606/41; 604/114
(58) Field of Search ...................... 606/32, 34, 41, 606/42, 49; 607/99, 105, 113; 604/114

(56) References Cited

U.S. PATENT DOCUMENTS

| 4,998,933 | A | * | 3/1991 | Eggers et al. ............... 606/41 |
| 5,098,431 | A | | 3/1992 | Rydell |
| 6,141,576 | A | * | 10/2000 | Littmann et al. ........... 600/381 |
| 6,179,824 | B1 | * | 1/2001 | Eggers et al. ............... 604/28 |
| 6,327,505 | B1 | | 12/2001 | Medhkour et al. |

* cited by examiner

*Primary Examiner*—Lee Cohen
(74) *Attorney, Agent, or Firm*—Girma Wolde-Michael; Michael C. Soldner (57) ABSTRACT

The present invention provides an apparatus method for performing rf intraluminal reduction and/or occlusion with a virtual electrode. An apparatus in accord with the present invention includes a catheter and a guide wire. The guide wire includes a conductive core having a proximal end electrically connected to a generator of rf current and an exposed distal end. An insulative material having disposed therein at least one microlumen for providing a conductive fluid to a target site within the lumen encases the guide wire.

18 Claims, 8 Drawing Sheets

APPARATUS FOR RF INTRALUMINAL REDUCTION AND OCCLUSION

CROSS-REFERENCE TO RELATED APPLICATIONS

This application is a division of U.S. application Ser. No. 09/304,681, filed May 4, 1999, now U.S. Pat. No. 6,327,505, which claims the benefit of U.S. Provisional Application No. 60/084,580, filed on May 7, 1998.

FIELD OF THE INVENTION

The present invention relates generally to an apparatus and a method for the treatment of intraluminal conditions, including but not limited to vascular abnormalities, fallopian tubes for purposes of sterilization, and bronchioles for purposes of lung volume reduction, using electrical energy. More particularly, the present invention relates to the intraluminal closure of vessels and other body lumens through the application of radio frequency electrical current and a conductive fluid to create a virtual electrode for passage of electrical current into tissue.

BACKGROUND OF THE PRESENT INVENTION

Humans are beset with a variety of vascular abnormalities, among them arteriovenous malformations, arteriovenous fistulas, and aneurysms. Two very serious cerebral vascular ailments are arteriovenous malformations and aneurysms. Arterial-venous malformations, commonly referred to as AVMs, are a fibrous mass of intertwined, directly connected arterial and venous vessels. That is, the artery will branch into numerous smaller arterial vessels that in turn feed directly into the numerous veins. An AVM located in the brain therefore deprives certain areas of the brain of the blood needed for proper functioning. As the AVM steals blood from normal brain parenchyma, the theft of blood can create a variety of disease states or brain malfunctions, including but not limited to epilepsy and transient ischemic attacks. One of the considerable risks associated with AVM growth is that the AVM will burst, leading to intracerebral bleeding.

An aneurysm is an abnormal bulge in the wall of a blood vessel that develops as a result of a weakness in the vessel wall. Aneurysms can take two forms: sacular and fusiform wherein a portion of or the entire circumferential extent of the vessel wall is implicated, respectively. Aneurysms can rupture, leading to cerebral bleeding and can cause a patient to have a stroke or to die. An arteriovenous fistula is a direct fluid connection between an otherwise fluidically isolated artery and vein.

A number of techniques and procedures have been developed to deal with AVMs and aneurysms. Both have been treated through surgery. During a surgical procedure to treat an AVM, the skull is opened and the feeding arteries and outgoing veins are ligated. The AVM is then excised. This procedure will normally require some cutting and removal of brain tissue. In addition, there have been several minimally invasive procedures developed to treat these vascular ailments. For example, AVMs have been treated by inserting a catheter into a patient and guiding it to the location of the AVM. A glue is then released that forms a plug and blocks the artery feeding the AVM. The blood is diverted back into the normal blood flow path as a result.

Aneurysms have also been treated by various techniques. Surgical treatment of an aneurysm will typically involve exposing the aneurysm and then applying a clip to the neck of the aneurysm to close off the aneurysm from the vessel, thereby re-establishing normal circulating blood flow in the treated vessel. One minimally invasive procedure involves delivering a catheter to the point of the arterial or venous aneurysm and then releasing a coiled wire into the aneurysm itself. Once released, the wire uncoils to fill the aneurysm. Blood tends to clot around the coiled wire, thus sealing off the aneurysm. Another minimally invasive procedure, known as Hunterian ligation, involves placing a detachable balloon via a catheter at the location of the aneurysm, inflating the balloon, and then releasing it, thereby completely occluding the artery. Yet another minimally invasive procedure involves placing a detachable balloon inside the aneurysm itself, inflating it and detaching it.

While effective, the prior known techniques of treating vascular ailments, particularly cerebral vascular ailments, carries with them certain risks that are preferably avoided. For example, open cranial surgery carries with it risks of infection, hemorrhaging, anesthetic risks, organ function failure, stroke, paralysis and death. Minimally invasive procedures like treatment of AVMs with glue can be difficult because the blood flow through the AVM will inhibit the solidification of the glue at the proper location. In addition, the glue plug may loosen or dissolve over a time, leading to the reoccurrence of the AVM, that is, the recanalization or reopening of the previously occluded vessel. As for treating an aneurysm with a coiled wire, the wire is left in the brain in the midst of a forming clot. The clot or portions thereof can break away into the blood stream and can cause a stroke. In addition, the coiled wire has been known to spontaneously dislodge and migrate through the vascular system. Likewise, the use of a balloon to treat an aneurysm has its share of risks, among them premature balloon detachment, rupture after inflation and detachment, and migration. Migration can lead to an unexpected and undesired distal vessel occlusion, which can in turn lead to brain ischemia and ischemic stroke.

In summary, treatment of vascular abnormalities presently involves either surgical intervention or minimally invasive procedures that in some situations operate to occlude the vasculature (AVMs) and in others to occlude the abnormality itself (aneurysms). Both procedures offer the possibility of severe risks, however.

It has recently been proposed to use radio frequency electrical current for intraluminal procedures. U.S. Pat. No. 5,098,431 to Rydell is an example of such proposed use. Such proposals involve insertion of a current carrying guide wire into a lumen and then energizing the exposed electrode. As the current passes from the electrode, the surrounding luminal fluid is heated as well as the lumen wall. As the temperature of the fluid and lumen increases, the cells in the lumen wall begin to dry, leading to possible rupture of the cell walls. In this manner, the lumen could be severed. This use thus corresponds to electrocautery. The effects on the lumen with this procedure are difficult for the surgeon to control.

Reduction, restriction, or occlusion of the various lumens being treated with radio frequency (rf) electrical energy coupled to the lumen walls with a virtual electrode, would reduce or eliminate some or all of the foregoing risk factors. In this procedure, a conductive solution is introduced into the site where it is desired to affect the tissue. An electrical current is then supplied to the conductive fluid via a metal electrode electrically coupled to an rf current generator to create a virtual electrode. The virtual electrode spreads the supplied current to the walls of the vessel. Typically, the greatest resistance or impedance to the flow of the rf current will be at the interface between the virtual electrode and the vessel walls, leading to initial heating at the site of the interface, that is, the vessel walls. Stated otherwise, the vessel walls have a greater resistance to the passage of current and like all non-superconducting materials begins to heat as the rf current is supplied.

As the resistance of the vessel walls leads to heating, the temperature of the vessel walls begins to rise and the connective tissues found in the vessel walls begin to depolymerize and shrink, causing the vessel to collapse inwardly in a radial direction and to shorten in a longitudinal direction. In this manner, then, a vessel, a segment or wall portion of a vessel, or other body lumen or segment or portion thereof such as a blood vessel, fallopian tube or bronchiole, could be shrunk as desired to the point of being completely occluded.

It would be desirable to have an apparatus and method for treating vascular ailments, in particular cerebral vascular ailments, and for performing other intraluminal procedures, that is not subject to the foregoing disadvantages, that can be performed using minimally invasive surgical techniques, that will provide a permanent solution to the ailment or treatment to the condition being affected, and that is safer than prior known techniques for treating such ailments.

SUMMARY OF THE INVENTION

It is an object of the present invention to provide a new and improved apparatus that is not subject to the foregoing disadvantages.

It is another object of the present invention to provide an apparatus that can shrink the elements of connective tissues forming the walls of a body lumen.

It is still another object of the present invention to provide a method of partially or totally occluding a lumen or segment of a lumen using rf current and a virtual electrode.

The foregoing objects of the present invention are provided by an apparatus and method for performing rf intraluminal reduction and/or occlusion with a virtual electrode. An apparatus in accord with the present invention includes a catheter and a guide wire having, in one preferred embodiment, multiple segments of differing flexibility. The guide wire includes a conductive core having proximal and distal ends thereof. A first segment of the guide wire located at the most distal end thereof is exposed for the passage of radio frequency electrical current therefrom, thereby providing an electrode. An insulative material preferably formed of biocompatible polymers encases the guide wire from substantially the proximal end thereof to the first segment. In one preferred embodiment, the distal end of the insulative material includes varying thicknesses thereof to provide a varying flexibility to the distal end of the guide wire. For example, a guide wire in accord with the present invention may include a first insulated segment that has an insulative coating having a first radius and a second insulated segment located proximally of the first insulated segment that has a second radius that is greater than the first. Other segments having additional varying thicknesses may be included. Disposed within the insulating layer and extending substantially the entire length of the guide wire is at least one lumen for providing a conductive or electrolytic fluid to the target treatment site to form the virtual electrode.

A catheter that may be used with the present invention may include one or more lumens disposed in the catheter wall thereof. Such lumens may be used, for example, to provide an angiographic solution, an angioscope, and suction to a reduction/occlusion site.

In a method in accord with the present invention, a flow path for providing an rf conductive solution to a target treatment site in a body lumen is introduced into the body lumen. The conductive solution is delivered and an electrode is introduced into the lumen at the target reduction/occlusion site either simultaneously or subsequent to the introduction of the flow path for the conductive fluid. Typically, though not in all cases, the conductive fluid will be infused prior to the initiation of the rf current. Such pre-infusion is helpful where the lumen reduction is occurring in a vessel filled with blood. The conductive fluid that is pre-infused will displace luminal fluid, such as blood, for example, which will usually be less conductive than the conductive fluid, at the target treatment area in the lumen. Radio frequency current is applied to the target site by a conductive electrode that is electrically connected to an rf power source through the conductive fluid, causing the connective tissues, such as but not limited to collagen and smooth muscle cells, in the lumen walls to heat and contract. Application of the rf current is discontinued when the lumen wall has contracted or been reduced to the desired extent, which will often be complete occlusion. Typically, to provide a permanent occlusion of the lumen, such as when an AVM is treated, the method will include the step of withdrawing proximally the conductive electrode, which typically will be made of a metal or metal alloy, during the application of rf power, and thus the virtual electrode, thus collapsing the lumen not only radially but longitudinally along its extent. Normally, the infusion will continue throughout the entire period of time that rf power is being supplied to the treatment site and will be discontinued only after the rf power has been discontinued.

The foregoing objects of the invention will become apparent to those skilled in the art when the following detailed description of the invention is read in conjunction with the accompanying drawings and claims. Throughout the drawings, like numerals refer to similar or identical parts.

DETAILED DESCRIPTION OF THE INVENTION

Figure 1:
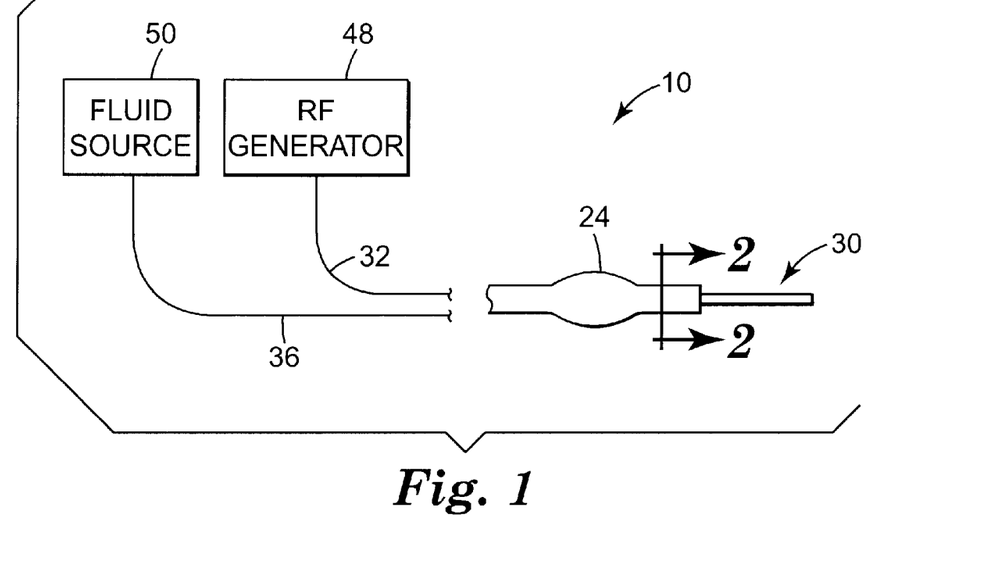
FIG. 1 is an illustration of an apparatus in accord with the present invention.
Figure 2:
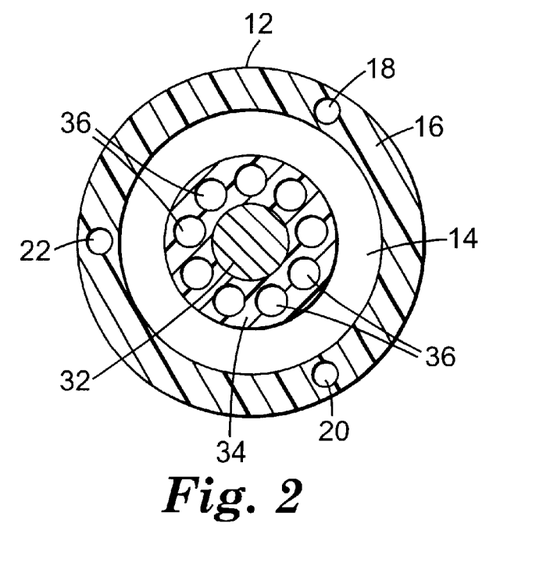
FIG. 2 is a cross-sectional view of the apparatus shown in FIG. 1 taken along viewing plane 2—2 thereof.

An apparatus 10 in accord with the present invention is illustrated in FIGS. 1–4. Thus, apparatus 10 includes a catheter 12 including an interior lumen 14 disposed centrally therein. Typically, though not critical to the present invention, lumen 14 will be centrally disposed with respect to a circular cross section of catheter 12. Catheter 12 preferably includes a wall 16 having a substantially annular cross sectional configuration. Wall 16 may include disposed therein and running substantially the length thereof at least one lumen useful for providing a variety of functions. Thus, as seen in FIG. 2, catheter 12 may include lumens 18, 20, and 22. Lumen 18 may be provided, for example, for providing a pathway for air or a liquid such as saline to inflate a balloon 24, which is useful for temporarily locating catheter 12 within a vessel as known in the art and for inhibiting or stopping the passage of fluid within a body lumen in which the apparatus 10 is disposed. Lumen 20 may be provided to provide a suction or vacuum source for the removal of fluid as desired by the physician, as known in the art. Finally, lumen 22 may be provided for use by an angioscope, again as known in the art.

Disposed within catheter 12 is a guide wire 30. It will be observed that guide wire 30 does not completely occlude catheter lumen 14, thus enabling the volume surrounding guide wire 30 to function, if desired, as an infusion/flush lumen for angiography. Guide wire 30 will be movable in a proximal B distal direction within catheter lumen 14.

Guide wire 30 preferably includes an electrically conductive wire 32 encased within a sheath 34 made of a non-conductive material. Sheath 34 will include therein at least one microlumen 36. Microlumen 36 may be used as an infusion lumen for the delivery of fluids, vacuum or suction, or other uses. In the present embodiment it is, contemplated that microlumens 36 may be used to supply a conductive or electrolytic fluid to the target site within a body lumen, such as a vascular abnormality as previously described or a fallopian tube, bronchiole, or other targeted area.

Figure 3:
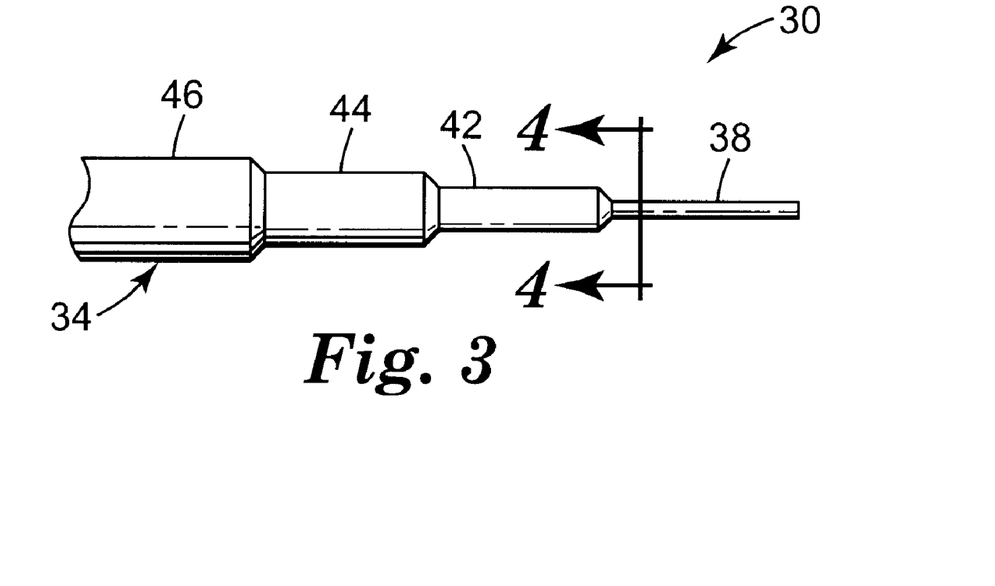
FIG. 3 is a view of the distal end of a guide wire for rf intraluminal reduction/occlusion in accord with the present invention.
Figure 4:
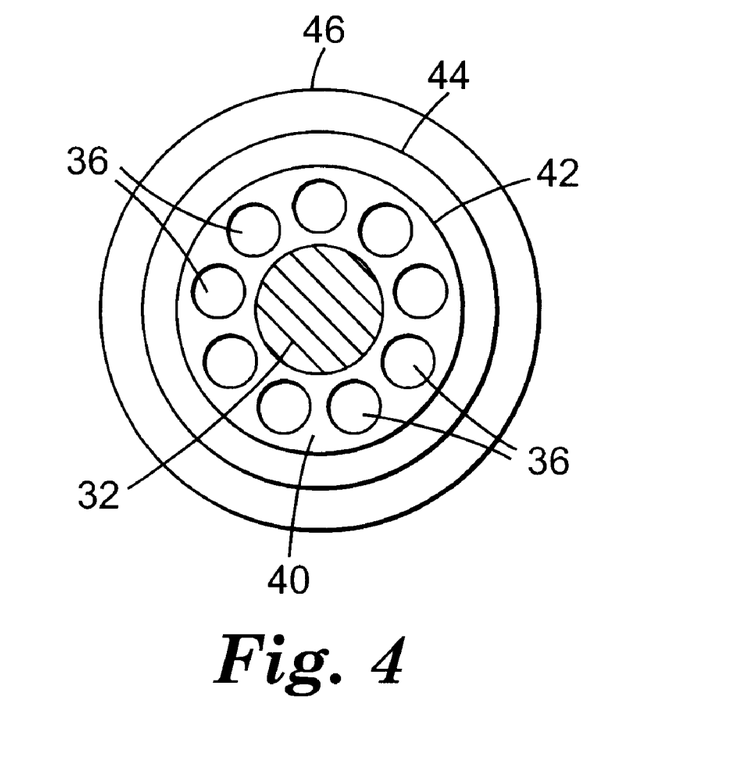
FIG. 4 is a cross sectional view of the guide wire of FIG. 3 taken along viewing plane 4—4 thereof.

Referring now to FIGS. 3 and 4, it will be observed that the distal end of the guide wire 30 includes an exposed wire or metal electrode 38. Electrode 38 may be formed of a solid wire, a wire mesh or braided material, or a coiled wire having either a circular or rectangular cross section, such as shown in FIGS. 12–15. Exposed wire electrode 38 extends from a distal end face 40 of sheath 34. Face 40 may be substantially flat but preferably will thicken in the proximal direction to provide a more gentle approach of the guide wire 30 to the vessel in which it is used.

It will be observed that sheath 34 thickens in radius as it extends from the face 40 to the proximal end of the catheter 34. As shown in FIGS. 3 and 4, sheath 34 has three distinct thickness segments, 42, 44, and 46. The varying thicknesses of sheath 34 provide varying degrees of flexibility or suppleness to the distal end of guide wire 30. This flexibility facilitates movement of guide wire 30 into position in the various body lumens, which in the case of the vasculature can include varied complex and sharp curves. Preferably, guide wire 30 will have at least two differing thicknesses to provide at least three different degrees of flexibility or suppleness.

Referring now to FIG. 1 again, it will be observed that guide wire 30 is electrically connected to a radio frequency current generator 48 and that microlumens 36 are fluidically connected to a conductive fluid source 50. Generator 48 and source 50 may be included within a single operating unit controlled by a microprocessor or computer in accord with the present invention.

It will be understood that the dimensions of apparatus 10 will vary with the intended use thereof. For example, treatment of small cerebral vessels will require a device appropriately sized. Where apparatus 10 is to be used in body lumens larger than a cerebral vessel, such as a fallopian tube, the dimensions will naturally be larger.

Figure 5:
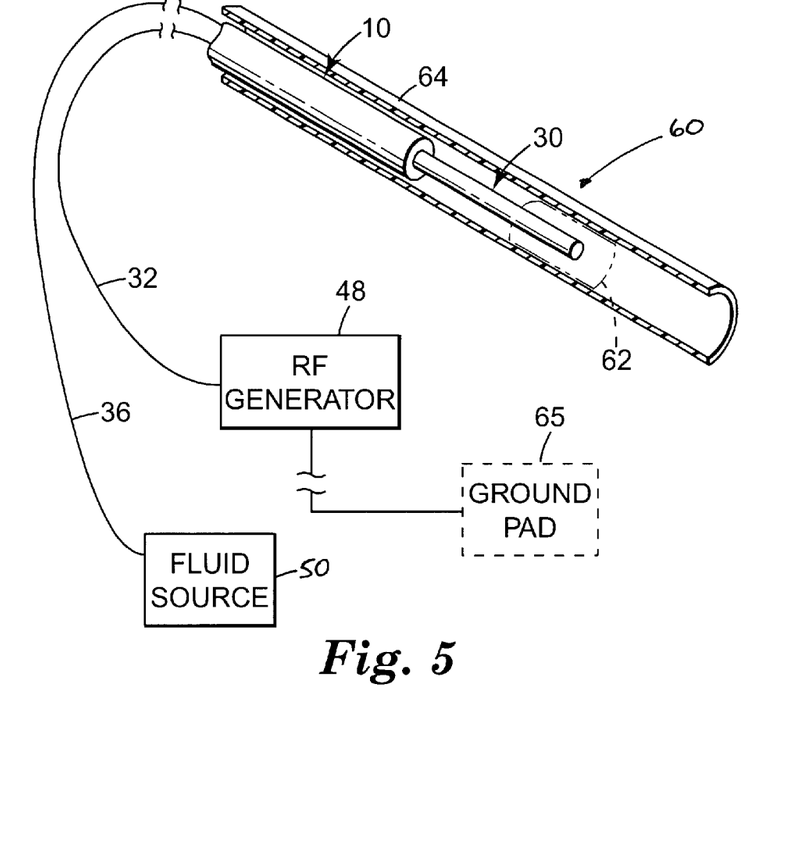
FIGS. 5–7 illustrate a method of occluding a lumen in accord with the present invention.
Figure 6:
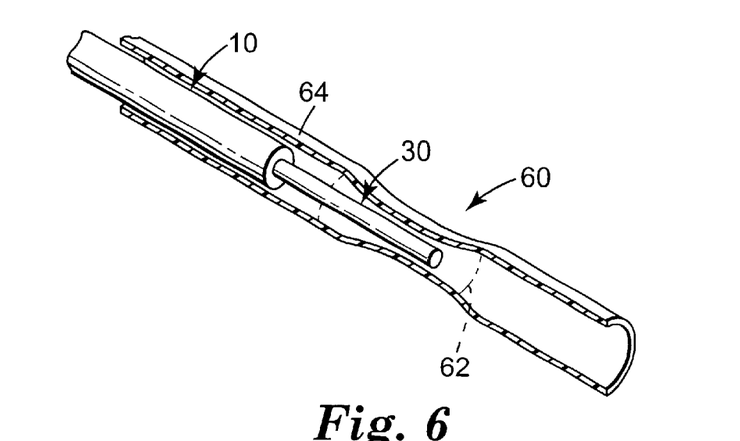
Figure 7:
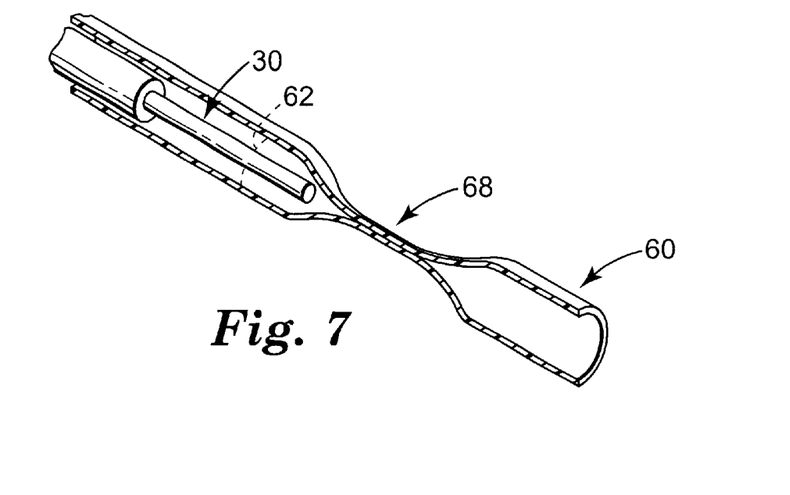

A method of treating a lumen in accord with the present invention is explained relative to FIGS. 5–7. In FIG. 5, apparatus 10 is shown in place within a body lumen 60 whose occlusion is desired. Located distally of the distal end (or electrode) 38 of the guide wire 30 may be an AVM if the lumen 60 is a cerebral vessel for example. Or lumen 60 may be a fallopian tube whose occlusion is desired for, for example, sterilization. As is known in minimally invasive procedures, typically apparatus 10 will be introduced to lumen 60 from a distant body location. For example, for certain cerebral vascular procedures, catheter 12 will be introduced into the femoral artery and moved to the proper location in the brain through navigation in the arterial system. As indicated by the dashed lines at 62, a conductive or electrolytic solution, such as isotonic or hypertonic saline, by way of example only, will be provided to the lumen 60 by apparatus 10 from fluid source 50. An rf current will then be provided to conductive fluid 62, which will resultingly act as a virtual electrode to couple energy to a wall 64 of the lumen 60. It will be understood that where a monopolar electrode is being used, a ground pad 65 (shown only in phantom and only in FIG. 5 for ease of illustration) may be placed adjacent to the patient=s body (not shown) to provide a return current flow path for the rf current from the electrode 38 to the rf current source 48. The present invention could also be used with a bi-polar electrode. As the wall 64 heats due to the inherent resistance thereof to the passage of the rf current, the connective tissues in the cells of the lumen wall 64 will begin to shrink, causing the lumen 60 to collapse or shrink radially inwardly in the area represented at 66, in FIG. 6. In addition, there will be a shrinkage of the lumen wall 64 in a longitudinal direction for the same reasons as given for the radial collapse.

Referring to FIG. 7, it will be observed that to avoid collapsing of the lumen 60 onto the guide wire 30, that guide wire 30 may be withdrawn slowly in the proximal direction. Should lumen 60 collapse onto guide wire 30, then it will be occluded only as long as the guide wire 30 remains in place. The subsequent withdrawal of the guide wire 30 will, in many instances, itself reopen or cause the reopening of the lumen 60. In addition, in many if not most applications of the present invention, it will be desired to collapse lumen 60 for a predetermined extent to reduce or eliminate the chance that lumen 60 will reopen. In such a circumstance, by slowly withdrawing guide wire 30 while continuing to provide conductive fluid within lumen 60 and rf current thereto, lumen 60 can be collapsed for an arbitrary distance at the discretion of the surgeon.

It will be observed that lumen 60 has shrunk or collapsed radially to such an extent that lumen 60 has been completely occluded in the area represented at 68. If lumen 60 were a cerebral artery feeding an AVM for example, then this procedure would result in the permanent closing of the feeding artery and allow the blood that had previously fed the AVM to be diverted to other, healthy brain tissue including that previously being starved of blood by the AVM. If lumen 60 were a fallopian tube, then the fallopian tube would have collapsed during the procedure, resulting in the sterilization of the woman undergoing the procedure.

It will be understood that conductive or electrolytic fluid will be delivered substantially continuously during the time that the rf current is being applied to the virtual electrode 62.

Figure 8:
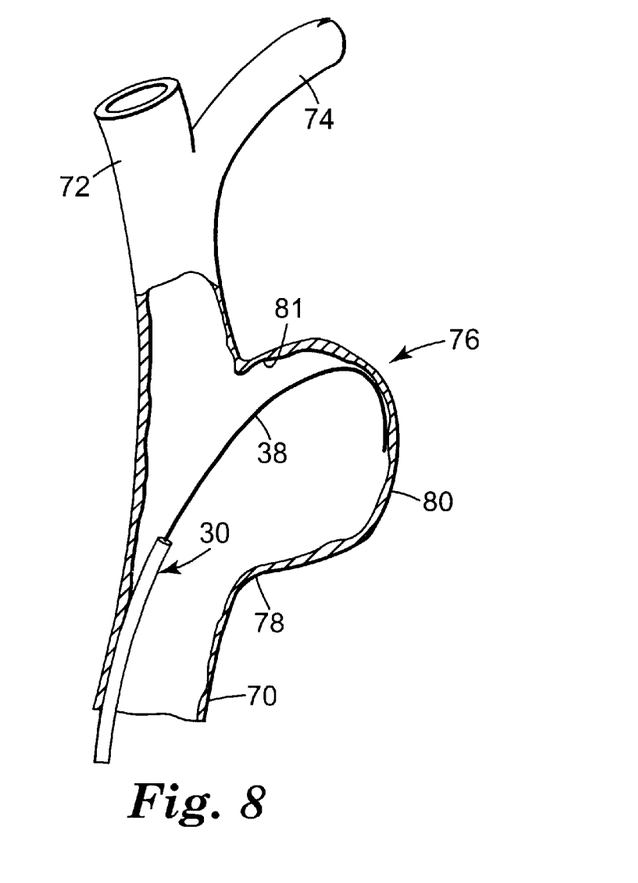
FIGS. 8–9 illustrate a method of treating a sacular aneurysm in accord with the present invention.
Figure 9:
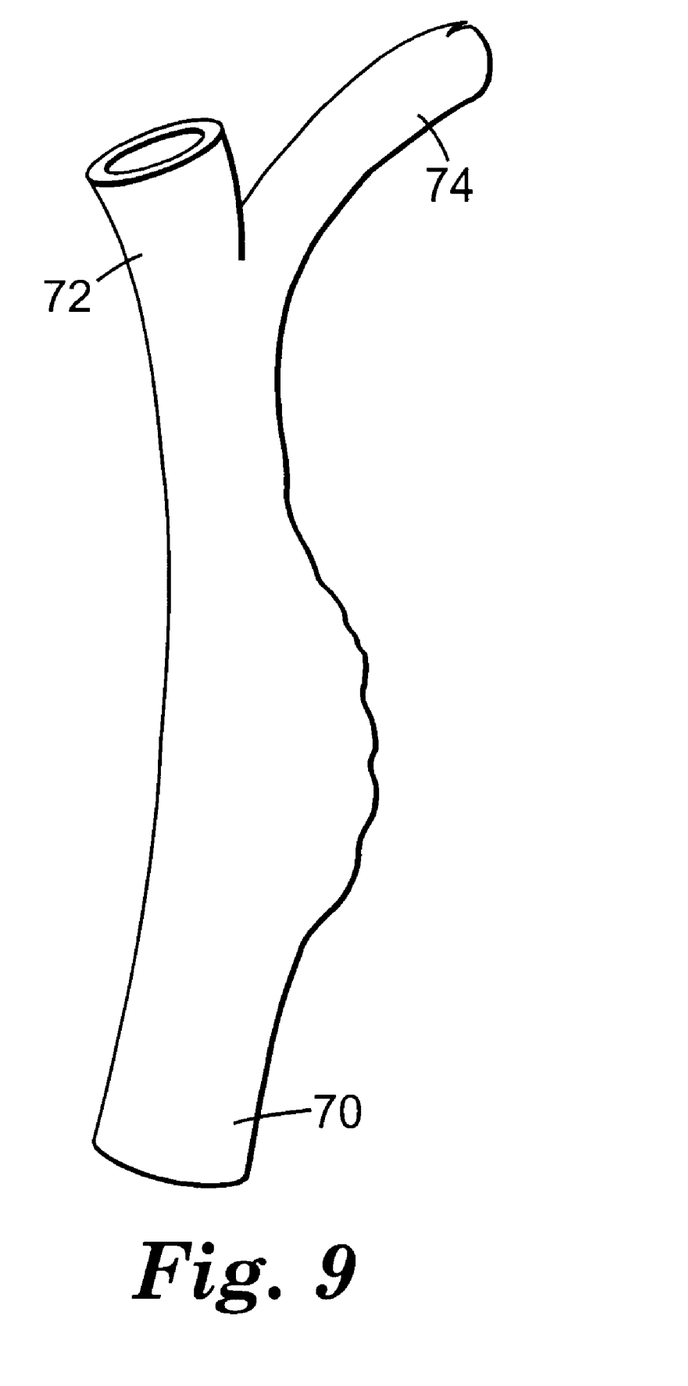

Turning to FIGS. 8–9, the use of the present invention to treat a sacular aneurysm will be explained. Thus, in the Figures it will be observed that a vessel 70 branches into smaller vessels 72 and 74. A sacular aneurysm 76 is shown located just prior to the branching of vessel 70 into vessels 72 and 74. Sacular aneurysm 76 has a neck 78 and an aneurysm wall 80.

In a method of treatment in accord with the present invention, a catheter 12 (not shown) will be inserted into the vascular system remotely from the aneurysm location, such as the femoral artery. Catheter 12 will be maneuvered close to the aneurysm location and then guide wire 30 will be extended therefrom. Electrode 38 is guided or steered into sacular aneurysm 76 through the neck 78. As electrode 38 enters the aneurysm 76 it will encounter an inner surface 81 of the aneurysm wall 80. Due to the flexibility of the electrode 38, electrode 38 will tend to curve backwards upon itself along inner vessel wall 81 as seen in the Figures. Once it has been determined that electrode 38 is disposed closely adjacent to or is lying against aneurysm inner surface 81, the infusion of conductive fluid will begin to wash out the blood within aneurysm 76. After a predetermined infusion period, rf current will be supplied to electrode 38 in the manner hereinbefore previously described. The physiological effects on the wall 80 will be as previously described, with the heat engendering a shrinkage of the connective tissues in the cells forming aneurysm wall 80 of aneurysm 76. This shrinkage will cause the aneurysm 76 to shrink or collapse inwardly toward vessel 70, returning vessel 70 to a normal or more normal state, re-establishing normal blood flow within vessel 70, and reducing or eliminating the likelihood of rupture of aneurysm 76.

Figure 10:
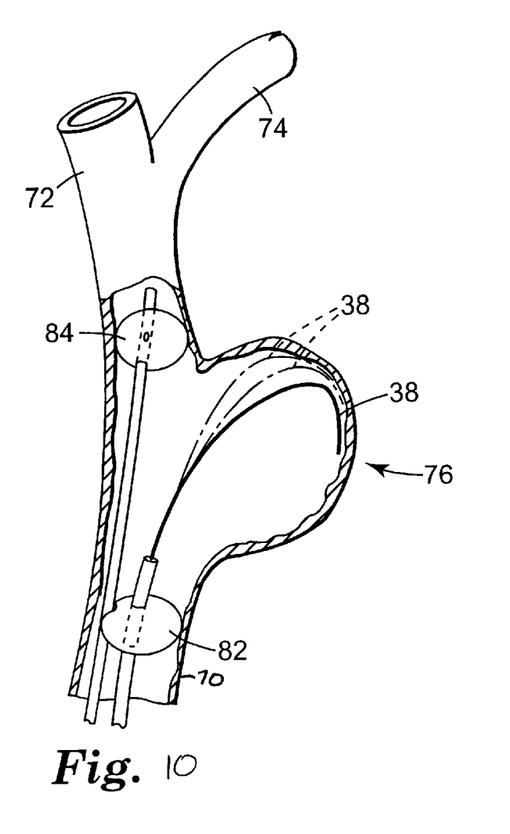
FIG. 10 illustrates treatment of an aneurysm according to the present invention using a dual balloon catheter system.

Referring to FIG. 10, an alternative embodiment of the present invention is used to treat an aneurysm 76 with a dual balloon catheter system. In this method, a first balloon 82 is inflated proximally of the electrode 38 to halt blood flow into aneurysm 76. A wash, which could comprise the conductive fluid, will then be dispensed by the catheter (not shown) to wash the blood within vessel 70 away. A second balloon 84 will then be inflated distally of electrode 38 and the conductive fluid will be dispensed to fill the vessel 70 between the balloons 82 and 84, including aneurysm 76, with conductive fluid. Electrode 38 can then be positioned, or it could be positioned prior to inflation of one or both balloons 82, 84 within aneurysm 76 as previously described. The rf power can then be initiated and aneurysm 76 shrunk as previously described. As shown in FIG. 10, electrode 38 may be maneuvered to various locations within aneurysm 76 to effectuate more complete shrinkage. After aneurysm 76 has been shrunk to the desired extent, balloons 82, 84 will be deflated and retracted along with guide wire 30.

Figure 11:
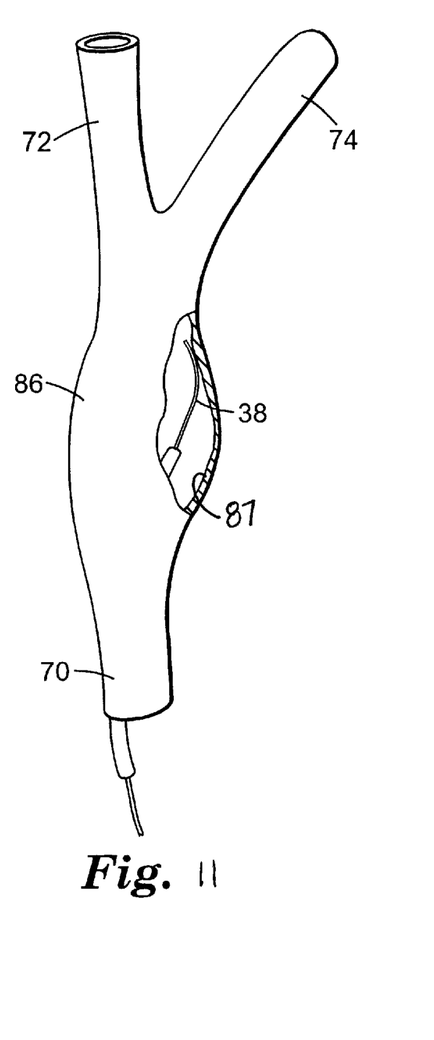
FIG. 11 illustrates treatment of a fusiform aneurysm according to the present invention.

Referring now to FIG. 11, a method of treating a fusiform aneurysm will be described. Thus, as shown in the Figure, vessel 70 includes a fusiform aneurysm 86. In this procedure, electrode 38 will be disposed against an inner wall 87 of aneurysm 86 and current will be applied to shrink the connective tissues in the area of power application. When a desired amount of shrinkage has occurred, electrode 38 will be repositioned and current will be reapplied. Electrode 38 will be moved around aneurysm 86 until the desired amount of shrinkage has occurred throughout the circumferential extent of aneurysm 86.

It will be understood that in treatment of AVMs, then, that the vessel is preferably completely occluded. The treatment of aneurysms, on the other hand, will normally not require complete occlusion of the lumen and may not in fact be desirable in many instances. Where the body lumen being treated is a fallopian tube, either a complete occlusion or a reduction in tube diameter sufficient to prevent passage of the egg would be sufficient. Where complete occlusion of the fallopian tube or other body lumen is not deemed desirable, then the dual balloon catheter method of treatment outlined relative to FIGS. 10 and 11 could be used.

In addition to the foregoing uses, the apparatus 10 could also be used to treat fistulas by reducing the size of the hole forming the fistula. Other intraluminal uses for the present invention include collapsing varicose veins and bronchioles.

Figure 12:
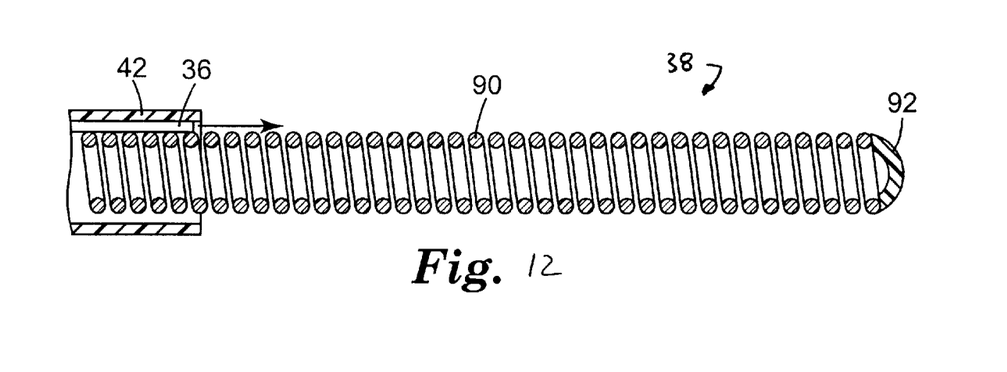
FIGS. 12–15 illustrate alternative embodiments of an active electrode for use in accord with the present invention.

Referring now to FIGS. 12–15, alternatives for electrode 38 will be described. FIG. 12 illustrates an electrode 38 formed from a wire coil 90 that is closed at a distal end 92 thereof by any known means. If desired, to manipulate the flexibility of coil 90 one or more adjacent coils could be attached to each other at selected positions along the exposed length thereof. In this one embodiment, microlumen 36 is adjacent wire coil 90, formed by sheath 34 (segment 42 of which is depicted in FIG. 12).

Figure 13:
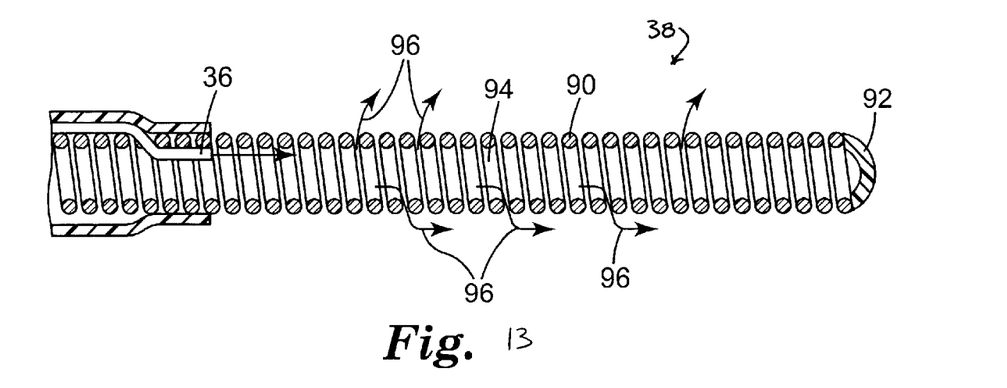

FIG. 13 shows another alternative embodiment of the distal end portion (or electrode) 38 of guide wire 30. In this embodiment at least one microlumen 36 is fed into an interior passage 94 of coil 90 by passing it between individual coils thereof. The conductive or electrolytic fluid would thus empty from a distal end of microlumen 36 into coil 90. The pressure head of the fluid would force the fluid between the individual coils as indicated by arrows 96 and out into the lumen of the vessel to be treated. As with the coil 90 shown in FIG. 12, if desired, to manipulate the flexibility of coil 90 of FIG. 13 and/or to control the distribution of the conductive fluid, one or more adjacent coils could be attached to each other at selected positions along the exposed length thereof.

While coil 90 has been shown as being formed of a wire having a circular cross section, it will be understood that a wire having a rectangular cross section could also be used in accord with the present invention to form the coil.

Figure 14:
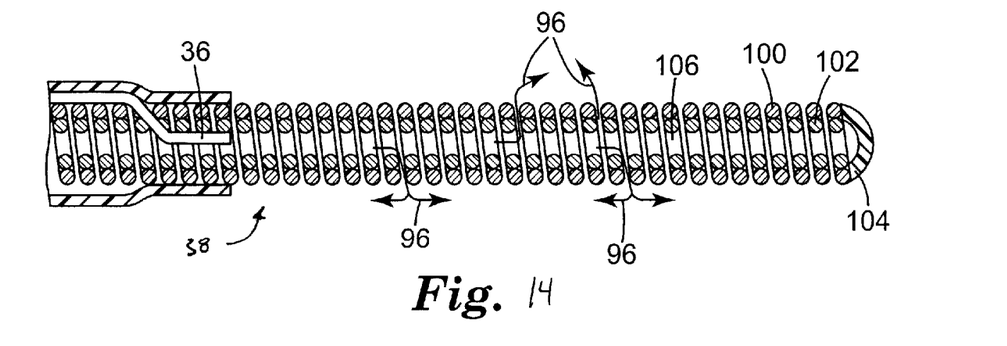

FIG. 14 illustrates yet another embodiment of the distal end of guide wire 30 wherein the electrode 38 is formed from a pair of concentrically engaged coils 100, 102, both of which are enclosed at the most distal end 104 as discussed relative to coil 90. As with the embodiment shown in FIG. 13, at least one microlumen 36 is fed into the interior passage 106 of the inner coil 102. The conductive fluid will empty from the microlumen 36 into the interior passage and under the influence of the pressure head provided by fluid source 50 (FIG. 5) will pass between the coils of coil 102 and coil 100 and into the lumen to be treated as indicated by arrows 96.

Figure 15:
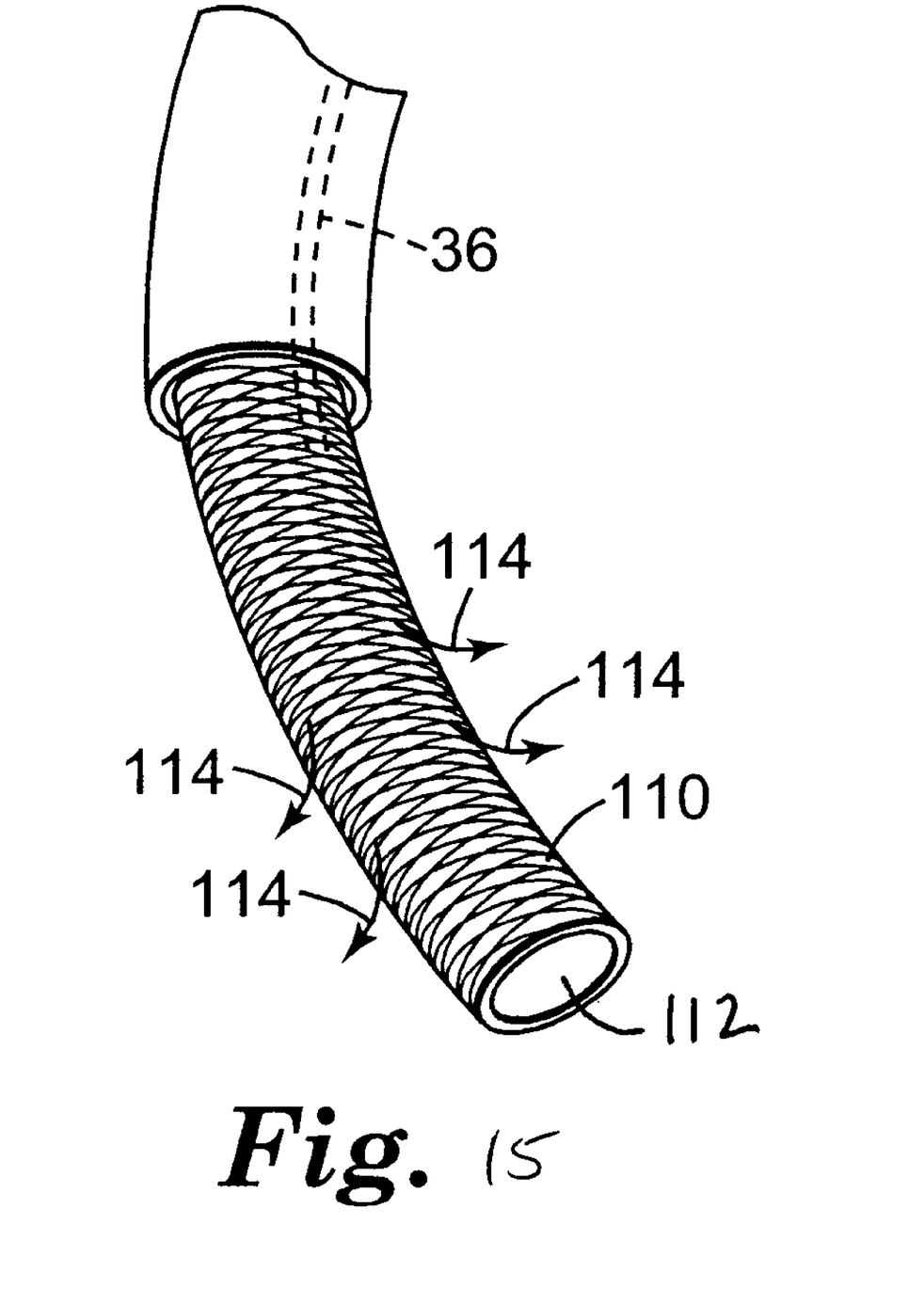

Referring now to FIG. 15, another embodiment of the distal end (or electrode 38) of the guide wire 30 is illustrated. In this embodiment, the exposed electrode 38 is formed of a wire or metal mesh or cloth 110. At least one microlumen 36 is fed into an interior (shown generally as 112) such that conductive fluid empties into interior 112. The conductive fluid will then flow between the wires forming the mesh or cloth as indicated by arrows 114.

It will be understood that the wire coils 90, 100, and 102 and the wire mesh 110 may extend proximally to the appropriate electrical connection to rf generator 48 (FIG. 5), or they may be attached in any known way to any other electrical conduit with just the active, uninsulated portion being formed thereby. For example, each of the coils 90, 100, and 102 and the wire mesh 110 could be electrically connected to a solid wire extending proximally to the rf generator 48.

The present invention having thus been described, other modifications, alterations, or substitutions may now suggest themselves to those skilled in the art, all of which are within the spirit and scope of the present invention. For example, it is presently contemplated that the coils 90, 100, and 102 and mesh 110 would comprise a biocompatible metallic material. The present invention is not so limited however, and any biocompatible conductive material having the appropriate flexibility could be used in lieu of a metallic material. It is therefore intended that the present invention be limited only by the scope of the attached claims below.

What is claimed is:

1. Apparatus for intraluminally reducing a body lumen defined by a wall at a target lumen reduction site, said apparatus comprising:
   a catheter having a lumen passage;
   a guide wire slidably movable within said lumen passage, said guide wire configured for intraluminal deployment within a body lumen and comprising:
   a conductor of electrical current; and
   an insulative layer surrounding said conductor substantially along the length of said conductor, said conductor having a most distal portion thereof exposed to provide an electrode and wherein said insulative layer of said guide wire includes at least one microlumen disposed therein for delivering an unrestrained conductive fluid to the target lumen reduction site to create a virtual electrode for coupling the electrical current to the wall of the body lumen.

2. The apparatus of claim 1 wherein said electrode comprises a conductive coil.

3. The apparatus of claim 2 wherein said conductive coil defines an interior passage and said at least one microlumen terminates in said interior passage and wherein the conductive fluid provided by said at least one microlumen flows into said interior passage and between said coils into the body lumen.

4. The apparatus of claim 1 wherein said electrode comprises a pair of concentrically wound conductive coils.

5. The apparatus of claim 4 wherein said conductive coils define an interior passage and said at least one microlumen terminates in said interior passage and wherein the conductive fluid provided by said at least one microlumen flows into said interior passage and between said coils into the body lumen.

6. The apparatus of claim 1 wherein said electrode comprises a conductive mesh.

7. The apparatus of claim 6, wherein said mesh is metal.

8. The apparatus of claim 6 wherein said mesh defines an interior passage and said at least one microlumen terminates in said interior passage and wherein the conductive fluid provided by said at least one microlumen flows into said interior passage and through said mesh into the body lumen.

9. The apparatus of claim 1 wherein said insulative layer includes a plurality of microlumens.

10. The apparatus of claim 1 wherein said insulative layer includes a plurality of longitudinally extending segments having varying radial thicknesses about said conductor, said radial thicknesses increasing in a proximal direction such that said guide wire is able to be manipulated through curvatures associated with the body lumen.

11. Apparatus for intraluminally shrinking at least a portion of the wall of a body lumen, said apparatus comprising:
   a catheter having a proximal end and a lumen passage;
   a guide wire having a distal end slidably movable within said lumen passage, said guide wire comprising:
   a conductor of electrical current; and
   an insulative layer surrounding said conductor substantially along the length of said conductor, said conductor having a most distal portion thereof exposed to provide an electrode, wherein said insulative layer includes a plurality of longitudinally extending segments having varying radial thicknesses about said conductor, said radial thicknesses increasing in a direction extending from the distal portion of the conductor to the proximal end of the catheter,
   whereby said varying radial thicknesses provide a varying degree of flexibility for said distal end of said guide wire such that said guide wire is able to be manipulated through curvatures of a lumen system to a target lumen reduction site within the body lumen, wherein said electrode is one of a conductive coil, a pair of concentrically wound conductive coils, or a wire mesh.

12. The apparatus of claim 11, wherein said mesh is metal.

13. Apparatus for intraluminally shrinking at least a portion of the wall of a body lumen, said apparatus comprising:
   a catheter having a proximal end and a lumen passage;
   a guide wire having a distal end slidably movable within said lumen passage, said guide wire comprising:
   a conductor of electrical current; and
   an insulative layer surrounding said conductor substantially along the length of said conductor, said conductor having a most distal portion thereof exposed to provide an electrode, wherein said insulative layer includes a plurality of longitudinally extending segments having varying radial thicknesses about said conductor, said radial thicknesses increasing in a proximal direction extending from the distal portion of the conductor to the proximal end of the catheter, whereby said varying radial thicknesses provide a varying degree of flexibility for said distal end of said guide wire such that said guide wire is able to be manipulated through curvatures of a lumen system to a target lumen reduction site within the body lumen, wherein said insulative layer includes a plurality of microlumens disposed therein for delivering a conductive fluid to the target lumen reduction site to create a virtual electrode for coupling rf current to the wall of the lumen.

14. The apparatus of claim 13, wherein said electrode comprises a plurality of conductive coils.

15. The apparatus of claim 14, wherein said plurality of conductive coils define an interior passage and at least one of said microlumens terminates in said interior passage and wherein the conductive fluid provided by said at least one microlumen flows into said passage and between said plurality of conductive coils into said lumen.

16. The apparatus of claim 15, wherein said electrode comprises a pair of concentrically wound conductive coils.

17. The apparatus of claim 13, wherein said electrode comprises a conductive mesh.

18. The apparatus of claim 17, wherein said mesh defines an interior passage and at least one of said microlumens terminates in said interior passage and wherein the conductive fluid provided by said at least one microlumen flows into said interior passage and through said mesh into said lumen.

* * * * *